(12) United States Patent
Ikariya et al.

(10) Patent No.: US 8,344,187 B2
(45) Date of Patent: Jan. 1, 2013

(54) PRACTICAL METHOD FOR REDUCING ESTERS OR LACTONES

(75) Inventors: Takao Ikariya, Tokyo (JP); Masato Ito, Kasuga (JP); Akira Shiibashi, Yokohama (JP); Takashi Ootsuka, Kawagoe (JP)

(73) Assignees: Tokyo Institute of Technology, Tokyo (JP); Central Glass Company, Limited, Ube-shi (JP)

( * ) Notice: Subject to any disclaimer, the term of this patent is extended or adjusted under 35 U.S.C. 154(b) by 215 days.

(21) Appl. No.: 12/991,073

(22) PCT Filed: Jun. 26, 2009

(86) PCT No.: PCT/JP2009/061682
§ 371 (c)(1),
(2), (4) Date: Nov. 4, 2010

(87) PCT Pub. No.: WO2010/004883
PCT Pub. Date: Jan. 14, 2010

(65) Prior Publication Data
US 2011/0092747 A1    Apr. 21, 2011

(30) Foreign Application Priority Data

Jul. 8, 2008  (JP) ................................ 2008-177857
Jun. 25, 2009  (JP) ................................ 2009-150401

(51) Int. Cl.
*C07C 29/136*  (2006.01)
*C07C 29/149*  (2006.01)
(52) U.S. Cl. .......................... 568/885; 568/814; 568/864
(58) Field of Classification Search .................... 568/885
See application file for complete search history.

(56) References Cited

U.S. PATENT DOCUMENTS
2009/0023961 A1 * 1/2009 Chen et al. .................... 568/814

FOREIGN PATENT DOCUMENTS

| JP | 2004-509087 A | 3/2004 |
|---|---|---|
| WO | WO 02/22526 A2 | 3/2002 |
| WO | WO 2005/092825 A1 | 10/2005 |
| WO | WO 2006/106483 A1 | 10/2006 |
| WO | WO 2006/106484 A1 | 10/2006 |

OTHER PUBLICATIONS

Masato Ito, et al., "Catalytic Hydrogenation of Polar Organic Functionalities Based on Ru-mediated Heterolytic Dihydrogen Cleavage", Chem. Commun., 2007, pp. 5134-5142, The Royal Society of Chemistry 2007.
Lionel A. Saudan, et al., "Dihydrogen Reduction of Carboxylic Esters to Alcohols Under the Catalysis of Homogeneous Ruthenium Complexes: High Efficiency and Unprecedented Chemoselectivity", Catalytic Hydrogenation, Angew. Chem. Inst. Ed., 2007, pp. 7473-7476, vol. 46, Wiley InterScience.
Masato Ito, et al., "Hydrogenation of Aromatic Ketones Catalyzed by ($\eta^5$-$C_5(CH_3)_5$)Ru Complexes Bearing Primary Amines", Organometallics, 2001, pp. 379-381, vol. 20, 2001 American Chemical Society.
Masato Ito, et al, "Highly Efficient Chemoselective Hydrogenolysis of Epoxides Catalyzed by a ($\eta^5$-$C_5(CH_3)_5$)Ru Complex Bearing a 2-(Diphenylphosphino)ethylamine Ligand", Organometallics, 2003, pp. 4190-4192, vol. 22, 2003 American Chemical Society.
Masato Ito, et al., "Chemoselective Hydrogenation of Imides Catalyzed by Cp*Ru(PN) Complexes and its Application to the Asymmetric Synthesis of Paroxetine", J. Am. Chem. Soc., 2007, pp. 290-291, vol. 129, 2007 American Chemical Society.
International Search Report dated Aug. 11, 2009 (Form PCT/ISA/210) with English translation, including Form PCT/ISA/237 (Eight (8) pages).

* cited by examiner

*Primary Examiner* — Brian J Davis
(74) *Attorney, Agent, or Firm* — Crowell & Moring LLP

(57) ABSTRACT

Esters and lactones can be respectively reduced to alcohols and diols in the presence of the Group 8 (VIII) transition metal complex, base and hydrogen gas ($H_2$). An extremely practical reduction method can be provided by preferable combinations of the Group 8 (VIII) transition metal complex, the base, a used amount of the base, a pressure of hydrogen gas and a reaction temperature. This method is used in place of hydride reduction and is a useful method by which design of highly active catalysts can be relatively easily made while a high productivity can be expected.

6 Claims, No Drawings

PRACTICAL METHOD FOR REDUCING ESTERS OR LACTONES

TECHNICAL FIELD

This invention relates to a reduction method for esters and lactones, important as a production technique for intermediates of pharmaceuticals and agricultural chemicals.

Methods in which a hydride reducing agent such as lithium aluminium hydride and the like is stoichiometrically used are widely employed to reduce esters to alcohols (similarly to reduce lactones to diols). To the contrary, insufficient researches have been made on reduction with hydrogen gas ($H_2$) by using a transition metal as a catalyst, particularly a highly reproducible method of using a homogeneous catalyst (Non-patent Citation 1). Recently a hydrogenation using a homogeneous ruthenium complex has been reported; however, a characteristic ligand is required in order to exhibit a catalytic activity (Patent Citation 1 and Non-Patent Citation 2).

Group 8 (VIII) transition metal complex used in the present invention has been reported to be effective for reduction of ketones, epoxides and imides under coexistence of base and hydrogen gas (Non-patent Citations 3 to 5). However, no reporting has been made for application to esters and lactones which are largely difficult in reduction as compared with those substrates.

PRIOR ART CITATIONS

Patent Citations

Patent Citation 1: International Publication No. 2006/106484 pamphlet

Non-Patent Citation

Non-patent Citation 1: Chem. Commun. (Great Britain), 2007, p. 5134-5142
Non-patent Citation 2: Angew. Chem. Int. Ed. (Germany), 2007, Volume 46, p. 7473-7476
Non-patent Citation 3: Organometallics (United States of America), 2001, Volume 20, p. 379-381
Non-patent Citation 4: Organometallics (United States of America), 2003, Volume 22, p. 4190-4192
Non-patent Citation 5: J. Am. Chem. Soc. (United States of America), 2007, Volume 129, p. 290-291

SUMMARY OF INVENTION

An object of the present invention is to provide practical reduction methods for esters and lactones.

Methods of stoichiometrically using hydride reducing agent are not suitable for mass production because the reducing agent is expensive and required to be carefully treated, and is troublesome in after-treatment and provides much waste. Accordingly, reduction using hydrogen gas without such problems, particularly a method using a homogeneous catalyst and relatively easy to be scaled up toward industrialization is eagerly required.

Further, according to the present invention, it is required to design a highly active catalyst in order that objects of the present invention are esters and lactones which are largely difficult to be reduced. In such a case, there is much knowledge, in which it is advisable to select a metal complex whose ligand can be easily changed. Group 8 (VIII) transition metal complex to be used in the present invention is rightly provided with such a condition and preferable. However, it is not apparent at all as to whether a catalyst system derived from the metal complex is effective for reduction of esters and lactones. Making the availability of it apparent is the subject of the present invention.

The present inventors have made eager investigation on the above-mentioned subject. As a result, it has been newly founded that esters and lactones can be respectively reduced to alcohols and diols in the presence of Group 8 (VIII) transition metal complex, base and hydrogen gas.

First, as Group 8 (VIII) transition metal complex, "Fe, Ru or Os complex having cyclopentadienyl(Cp) group or 1,2,3,4,5-pentamethylcyclopentadienyl(Cp*) group; halogen, carbon monoxide, acetonitrile, phenyl isocyanide or triphenylphosphine; and bidentate ligand of nitrogen-nitrogen (N—N) or phosphorus-nitrogen (P—N)" can be used. It has been newly apparent that "Ru complex having Cp* group, halogen or acetonitrile, and bidentate ligand (P—$C_2$—N) in which phosphorus and nitrogen are linked through two carbons" is preferable, and particularly "Cp*RuCl[$Ph_2P(CH_2)_2NH_2$] (ph: phenyl group)" is more preferable.

Next, there is particularly no limitation for base, in which it has been newly apparent that hydroxide or alkoxide of alkali metal is preferable, and particularly alkoxide of alkali metal is more preferable.

Additionally, concerning a used amount of base, a large amount of base is used as compared with in case of reduction of ketones, epoxides and imides thereby accomplishing a desired reaction at a high efficiency. A preferable used amount of base is 15 to 90 moles relative to 1 mole of Group 8(VIII) transition metal complex.

Further, concerning the pressure of hydrogen gas, reduction is made at a high pressure as compared with that in reduction of ketones, epoxides and imides, thereby accomplishing a desired reaction at a high efficiency. A preferable pressure of hydrogen gas is from 3 to 7 MPa.

Lastly, concerning a reaction temperature, reduction is made at a high reaction temperature as compared with that in reduction of ketones, epoxides and imides, thereby accomplishing a desired reaction at a high efficiency. A preferable reaction temperature is from 80 to 150° C.

Thus, useful methods as practical reduction methods for esters and lactones have been found thereby reaching the present invention.

In other words, the present invention includes [Invention 1] to [Invention 6] and provides practical reduction methods for esters and lactones.

[Invention 1]

A method of respectively reducing esters represented by a general formula [2]

[chem.2]

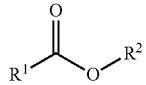

[2]

where $R^1$ is alkyl group, substituted alkyl group, alkenyl group, substituted alkenyl group, aromatic ring group or substituted aromatic ring group; and $R^2$ is alkyl group or substituted alkyl group, and lactones represented by a general formula [3]

[chem.3]

[3]

where R$^1$—R$^2$ indicates that R$^1$ and R$^2$ of the esters represented by the general formula [2] is bonded by a covalent bond, to alcohols represented by a general formula [4]

[chem.4]

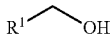

[4]

where R$^1$ is the same as R$^1$ of the esters represented by the general formula [2], and diols represented by a general formula [5]

[chem. 5]

[5]

where R$^1$—R$^2$ indicates that R$^1$ and R$^2$ of the esters represented by the general formula [2] is bonded by a covalent bond, in the presence of Group 8 (VIII) transition metal complex represented by a general formula [1]

[chem. 1]

AMBC  [1]

where A is cyclopentadienyl(Cp) group or 1,2,3,4,5-pentamethylcyclopentadienyl(Cp*) group; M is Fe, Ru or Os; B is halogen, carbon monoxide, acetonitrile, phenyl isocyanide or triphenylphosphine; and C is bidentate ligand of nitrogen-nitrogen (N—N) or phosphorus-nitrogen (P—N), base and hydrogen gas (H$_2$).

[Invention 2]

A method of reducing esters and lactones as described in Invention 1, characterized in that the Group 8 (VIII) transition metal complex represented by the general formula [1] is Group 8 (VIII) transition metal complex represented by a general formula [6]

[chem. 6]

C$p$*RuX(P—C$_2$—N)  [6]

where Cp* is 1,2,3,4,5-pentamethylcyclopentadienyl group; X is halogen or acetonitrile; P—C$_2$—N is bidentate ligand in which phosphorus and nitrogen are linked through two carbons, and the base is hydroxide or alkoxide of alkali metal.

[Invention 3]

A method of reducing esters and lactones as described in Invention 2, characterized in that the Group 8 (VIII) transition metal complex represented by the general formula [6] is Group 8 (VIII) transition metal complex represented by a general formula [7]

[chem. 7]

C$p$*RuCl[Ph$_2$P(CH$_2$)$_2$NH$_2$]  [7]

where Cp* is 1,2,3,4,5-pentamethylcyclopentadienyl group; Ph is phenyl group, and the base is alkoxide of alkali metal.

[Invention 4]

A method of reducing esters and lactones as claimed in any of Inventions 1 to 3, characterized in that a used amount of the base is from 15 to 90 moles relative to 1 mole of the Group 8 (VIII) transition metal complex.

[Invention 5]

A method of reducing esters and lactones, as claimed in any of Inventions 1 to 4, characterized in that a pressure of the hydrogen gas (H$_2$) is from 3 to 7 MPa.

[Invention 6]

A method of reducing esters and lactones, as claimed in any of Inventions 1 to 5, characterized in that a reaction temperature is from 80 to 150° C.

DETAILED DESCRIPTION

This invention can be applied to reduction of esters and lactones which are largely difficult to be reduced. Accordingly, this can be used in place of hydride reduction and therefore preferably used for mass production.

Concerning Group 8 (VIII) transition metal complex used in the present invention, there are hitherto much knowledge, and design of highly active catalysts can be relatively easily accomplished. Further, by making a change to bidentate ligand of optically active N—N or P—N, development to asymmetric synthesis can be expected. To the contrary, ruthenium complex disclosed in Patent Citation 1 and Non-patent Citation 2 makes its catalytic activity disappear upon a little change of ligand and therefore is limited in knowledge to be used for catalyst design.

Additionally, industrially important merits have been newly found. In a catalytic system derived from Group 8(VIII) transition metal complex, basic isopropyl alcohol is very effective for heterolitic dissociation of hydrogen gas. Consequently, isopropyl alcohol has been first selectively used as a reaction solvent. However, a variety of reaction solvents can be used in reduction of esters and lactones which are objects of the present invention. Accordingly, even for a substrate which is low in solubility to isopropyl alcohol, a reaction can be made at a high substrate concentration by selecting a reaction solvent, thereby making it possible to expect a high productivity. In practice, even if a reaction is made at a high substrate concentration as compared with reduction of ketones, epoxides and imides, a desired reaction can be made at a high efficiency. To the contrary, the following example has been reported: A reaction is made at a low substrate concentration by using a mixed solvent of isopropyl alcohol and tetrahydrofuran which assists solution, in reduction of imides which are low in solubility to isopropyl alcohol (Non-patent Citation 5).

Thus, the present invention is a practical reduction method which can be used in place of hydride reduction, in which design of highly active catalysts can be relatively easily achieved while a high productivity can be expected.

The practical reduction method for esters and lactones according to the present invention will be discussed in detail.

According to the present invention, esters represented by the general formula [2] and lactones represented by the general formula [3] can be respectively reduced to alcohols represented by the general formula [4] and diols represented by the general formula [5] in the presence of Group 8(VIII) transition metal complex represented by the general formula [1], base and hydrogen gas.

A of the Group 8(VIII) transition metal complex represented by the general formula [1] is Cp group or Cp* group, in which Cp* group is preferable.

M of the Group 8(VIII) transition metal complex represented by the general formula [1] is Fe, Ru or Os, in which Fe and Ru are preferable, in which particularly Ru is more preferable.

B of the Group 8(VIII) transition metal complex represented by the general formula [1] is halogen such as chlorine, bromine and iodine or the like, carbon monoxide, acetonitrile, phenyl isocyanide or triphenylphosphine, in which halogen and acetonitrile are preferable, in which particularly chlorine is more preferable. According to kind of B, the form of cationic complex can be also taken, in which examples of counter-anion are chlorine, tetrafluoroborate ($BF_4-$), triflate ion ($CF_3SO_3-$), hexafluorophosphate ($PF_6-$), hexafluoroantimonate ($SbF_6-$) and the like, in which $CF_3SO_3-$, $PF_6-$ and $SbF_6-$ are preferable, in which $CF_3SO_3-$ and $PF_6-$ are particularly more preferable.

C of the Group 8 (VIII) transition metal complex represented by the general formula [1] is the bidentate ligand of N—N or P—N, in which P—$C_2$—N is preferable, in which particularly $Ph_2P(CH_2)_2NH_2$ is more preferable. The N—N bidentate ligand can be produced by a known method, and many of the N—N bidentate ligands can be commercially available in the market. The P—N bidentate ligand can be produced according to Aldrichimica ACTA (United States of America), 2008, Volume 41, Number 1, p. 15-26 and the like. Although typical bidentate ligands of N—N and P—N(P—$C_2$—N) are shown in [chem. 8] mentioned below, the bidentate ligand is not limited to these typical examples (substitution of an arbitrary number of lower alkyl groups may be made onto arbitrary carbon atoms in the structural formulae of the respective typical examples). Abbreviated symbols used in the typical examples are as follows: Me is methyl group, ph is phenyl group, i-Pr is isopropyl group, t-Bu is tert-butyl group, and Bn is benzyl group; * indicates asymmetric carbon or axial asymmetry and can take R-body or S-body; and if there are a plurality of *, any combination of R-body and S-body may be taken.

[chem. 8]

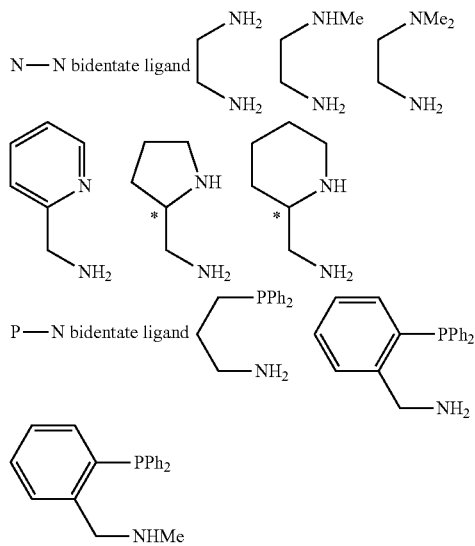

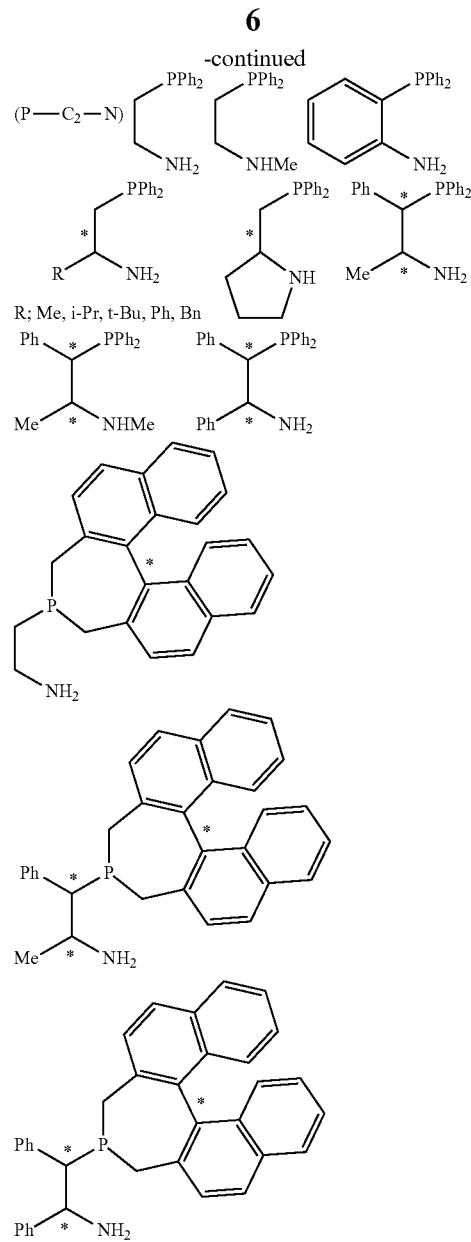

Additionally, P—N bidentate ligands described in the above-mentioned Aldrichimica ACTA can be also used.

The Group 8 (VIII) transition metal complex represented by the general formula [1] can be produced according to Non-patent Citation 4, Organometallics (United States of America), 1997, Volume 16, p. 1956-1961 and the like. While claims of the present invention are recited based on a binary preparation method in which the catalytic system is derived from AMBC and base, the claims of the present invention cover all methods in which the same catalytically active species {AMHC [where H is hydride]} can be prepared in a reaction system under the action (reaction solvent may participate in) with hydrogen gas. This will be specifically supplemented below. A catalytically active species of Cp*RuH[$Ph_2P(CH_2)_2NH_2$] prepared by the binary preparation method {Cp*RuCl[$Ph_2P(CH_2)_2NH_2$], base/hydrogen gas (reaction solvent may participate in)} can be similarly prepared by a ternary preparation method {Cp*RuCl(cod) (cod: 1,5-cyclooctadiene), $Ph_2P(CH_2)_2NH_2$, base/hydrogen gas (reaction solvent may participate in)}. Further, as reported in Non-patent Citation 4, the same catalytically active species {Cp*RuH[Ph$_2$P(CH$_2$)$_2$NH$_2$]} can be similarly prepared from Cp*RuCl[Ph$_2$P(CH$_2$)$_2$NH$_2$] and base in isopropyl alcohol. A reaction may be carried out in the presence of hydrogen gas (in coexistence of base if necessary) by using a previously prepared catalytically active species. It is meant that all preparation methods other than the specific example and having such a relation may also be covered by the claims of the present invention.

A used amount of the Group 8(VIII) transition metal complex represented by the general formula [1] may be a catalytic amount and therefore is usually preferably from 0.1 to 0.00001 mole, particularly more preferably from 0.05 to 0.0001 mole, relative to 1 mole of esters represented by the general formula [2] or lactones represented by the general formula [3].

The base is not particularly limited. Examples of the base are alkali metal hydrogen carbonate such as lithium hydrogen carbonate, sodium hydrogen carbonate, potassium hydrogen carbonate and the like; alkali metal carbonate such as lithium carbonate, sodium carbonate, potassium carbonate, cesium carbonate and the like; alkali metal hydroxide such as lithium hydroxide, sodium hydroxide, potassium hydroxide and the like; tetra-n-butyl ammonium hydroxide; alkali metal alkoxide such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide, potassium tert-butoxide and the like; organic base such as triethylamine, diisopropylethylamine, 1,8-diazabicyclo [5.4.0]undec-7-ene (DBU) and the like; lithium bis(trimethylsilyl)amide, sodium bis(trimethylsilyl)amide, potassium bis(trimethylsilyl)amide and the like. Of these, alkali metal hydroxide and alkoxide are preferable, in which particularly alkali metal alkoxide is more preferable.

A used amount of the base is sufficient to be not less than 1 mole relative to 1 mole of the Group 8(VIII) transition metal complex represented by the general formula [1], and preferably from 15 to 90 moles in order to effectively carry out a desired reaction, particularly more preferably from 20 to 80 moles upon taking practicality into consideration.

Concerning combination of the used amounts of the Group 8(VIII) transition metal complex represented by the general formula [1] and the base, the used amounts of the metal complex and the base are sufficient to be respectively a catalyst amount and more than the catalyst amount, and usually preferably respectively from 0.1 to 0.00001 mole and from 9 to 0.00015 mole, and particularly more preferably respectively 0.05 to 0.0001 mole and from 4 to 0.002 mole, relative to 1 mole of esters represented by the general formula [2] or lactones represented by the general formula [3].

A used amount of hydrogen gas (H$_2$) is sufficient to be not less than 2 moles relative to 1 mole of esters represented by the general formula [2] or lactones represented by the general formula [3], and usually preferably largely excessive and more preferably largely excessive under pressure. A pressure of hydrogen gas is sufficient to be higher than atmospheric pressure, and preferably from 3 to 7 MPa in order to effectively carry out a desired reaction and particularly more preferably from 4 to 6 MPa upon taking practicality into consideration.

$R^1$ of esters represented by the general formula [2] is alkyl group, substituted alkyl group, alkenyl group, substituted alkenyl group, aromatic ring group or substituted aromatic ring group, in which substituted alkyl group, substituted alkenyl group and substituted aromatic ring group are preferable, and particularly more preferably fluorine-substituted alkyl, alkenyl and aromatic ring groups.

Alkyl group has a carbon number of from 1 to 18 and can take linear or branched chain structure or cyclic structure (in case that the carbon number is not less than 3). Alkenyl group is arranged such that arbitrary single bonds each between adjacent two carbon atoms of the alkyl group are replaced with an arbitrary number of double bonds, in which the double bonds may take E-body, Z-body or mixture of E-body and Z-body in stereochemistry. Aromatic ring group has a carbon number of from 1 to 18 and may be aromatic hydrocarbon group such as phenyl group, naphthyl group, anthryl group or the like, or aromatic heterocycle group containing heteroatom such as nitrogen atom, oxygen atom, sulfur atom or the like, for example, pyrrolyl group, furyl group, thienyl group, indolyl group, benzofuryl group, benzothienyl group or the like.

The alkyl group, alkenyl group or aromatic ring group may have an arbitrary number of substituents on arbitrary atoms and with an arbitrary combination (corresponding to substituted alkyl group, substituted alkenyl group or substituted aromatic ring group, respectively). Examples of such substituents are halogen atom such as fluorine, chlorine, bromine and/or iodine; azide group; nitro group; lower alkyl group such as methyl group, ethyl group, propyl group and/or the like; lower haloalkyl group such as fluoromethyl group, chloromethyl group, bromomethyl group and/or the like; lower alkoxy group such as methoxy group, ethoxy group, propoxy group and/or the like; lower haloalkoxy group such as fluoromethoxy group, chloromethoxy group, bromomethoxy group and/or the like; lower alkylamino group such as dimethylamino group, diethylamino group, dipropylamino group and/or the like; lower alkylthio group such as methylthio group, ethylthio group, propylthio group and/or the like; cyano group; lower alkoxycarbonyl group such as methoxycarbonyl group, ethoxycarbonyl group, propoxycarbonyl group and/or the like; aminocarbonyl group (CONH$_2$); lower aminocarbonyl group such as dimethylaminocarbonyl group, diethylaminocarbonyl group, dipropylaminocarbonyl group and/or the like; alkynyl group; aromatic ring group such as phenyl group, naphthyl group, pyrrolyl group, furyl group, thienyl group and/or the like; aromatic ring oxy group such as phenoxy group, nap hthoxy group, pyrrolyloxy group, furyloxy group, thienyloxy group and/or the like; aliphatic heterocycle group such as piperidyl group, piperidino group, morpholinyl group and/or the like; protected hydroxyl group; protected amino group (including amino acid or peptide residue); protected thiol group; protected aldehyde group; protected carboxyl group; and/or the like.

In the present specification, the following terms are used to mean matters mentioned below: "lower" means linear or branched chain structure having carbon number of from 1 to 6, or cyclic structure (in case that carbon number is not less than 3) having carbon number of from 1 to 6. As "protective groups for hydroxyl group, amino group (including amino acid or peptide residue), thiol group, aldehyde group and carboxyl group", protective groups or the like described in Protective Groups in Organic Synthesis, Third Edition, 1999, John Wiley & Sons, Inc. may be used (two or more functional groups may be protected by one protective group). Additionally, to "alkynyl group", "aromatic ring group", "aromatic ring oxy group" and "aliphatic heterocycle group", substitution of halogen atom, azide group, nitro group, lower alkyl group, lower haloalkyl group, lower alkoxy group, lower haloalkoxy group, lower alkylamino group, lower alkylthio group, cyano group, lower alkoxycarbonyl group, aminocarbonyl group, lower aminocarbonyl group, protected hydroxyl group, protected amino group (including amino acid or peptide residue), protected thiol group, protected aldehyde group, protected carboxyl group, and/or the like may be made.

Since the present invention relates to reduction reaction, there is a case where substituent itself may be reduced according to kind of substituent. However, particularly in case of fluorine-substituted body, side reaction such as hydrogenolysis (reductive dehalogenation) or the like is difficult to occur, in which fluorine atom is introduced to α-position, β-position or γ-position of ester group thereby raising reaction rate. Further, substituted alkyl group whose α-position is substituted for fluorine atom and whose carbon number is not less than 2 (hydrogen atom also exists at α-position) hardly makes racemization under the reaction conditions of the present invention even by using optically active body. The thus obtained optically active fluorine-containing alcohols are important intermediates of pharmaceuticals and agricultural chemicals and therefore seem to be preferable substrates for the present invention.

$R^2$ of esters represented by the general formula [2] is alkyl group or substituted alkyl group, in which alkyl group is preferable, and particularly lower alkyl group is more preferable upon taking practicality into consideration. The alkyl group and the substituted alkyl group are respectively the same as alkyl group and substituted alkyl group described as $R^1$ of esters represented by the general formula [2].

$R^1$—$R^2$ of lactones represented by the general formula [3] indicates that $R^1$ and $R^2$ of the esters represented by the general formula [2] are bonded by a covalent bond. The covalent bond links arbitrary carbon atoms of $R^1$ and $R^2$ however, $R^1$ and $R^2$ may be linked through heteroatom such as nitrogen atom, oxygen atom or sulfur atom. Preferable $R^1$ and $R^2$ are the same as those in esters represented by the general formula [2].

Examples of the reaction solvent are aliphatic hydrocarbon family such as n-hexane, cyclohexane, n-heptane and the like; aromatic hydrocarbon family such as benzene, toluene, α,α,α-trifluorotoluene, xylene, ethylbenzene, mesitylene and the like; halogenated hydrocarbon family such as methylene chloride, chloroform, 1,2-dichloroethane and the like; ether family such as diethyl ether, 1,2-dimethoxyethane, 1,4-dioxane, tetrahydrofuran, 2-methyltetrahydrofuran, tert-butyl methyl ether, diisopropyl ether, diethyleneglycol dimethylether, anisole and the like; alcohol family such as methanol, ethanol, n-propyl alcohol, isopropyl alcohol, n-butyl alcohol, tert-butyl alcohol and the like; and the like. Of these, n-hexane, n-heptane, toluene, xylene, diethyl ether, 1,4-dioxane, tetrahydrofuran, methanol, ethanol, isopropyl alcohol and tert-butyl alcohol are preferable, in which particularly tetrahydrofuran and isopropyl alcohol are more preferable. These reaction solvents may be used singly or in combination. There is a case in which transesterification is made problematic when isopropyl alcohol is used for reduction of esters represented by the general formula [2]. In such a case, tetrahydrofuran may be preferably used. Further, in distillation for optically active 2-fluoropropanol [$CH_3C$*$HFCH_2OH$ (*: asymmetric carbon)] which is particularly important in optically active fluorine-containing alcohols as preferable objects of the present invention, tetrahydrofuran is easy to be separated from the reaction solvent as compared with isopropyl alcohol upon taking separation between optically active 2-fluoropropanol and the reaction solvent into consideration. To the contrary, isopropyl alcohol is preferable in reduction of lactones represented by the general formula [3].

A used amount of the reaction solvent is sufficient to be not less than 0.01 L (liter) and usually preferably from 0.05 to 2 L, and particularly more preferably from 0.1 to 1.5 L relative to 1 mole of esters represented by the general formula [2] or lactones represented by the general formula [3]. There is a case in which reaction rate lowers if reaction is carried out at a low substrate concentration. In such a case, the reaction rate can be raised by using a preferable amount of a reaction solvent.

A reaction temperature is sufficient to be not lower than 50° C., in which the reaction temperature is preferably from 80 to 150° C. in order to effectively carry out a desired reaction and particularly more preferably from 85 to 140° C. upon taking practicality into consideration.

A reaction time is not particularly limited, in which the reaction time is normally not longer than 72 hours; however, the reaction time varies according to catalytic system, substrate and reaction conditions, and therefore it is preferable to track the progressing status of a reaction by using analytical means such as gas chromatography, thin-layer chromatography, liquid chromatography, nuclear magnetic resonance or the like and to determine a time at which raw material is almost diminished as a terminal point of the reaction.

As after-treatment, normal operations are made on a reaction-completed liquid, thereby obtaining objective alcohols represented by the general formula [4] or diols represented by the general formula represented by the general formula [5]. The object may be purified to have a high chemical purity by activated carbon treatment, distillation, recrystallization, column chromatography and/or the like, if necessary.

According to the present invention, esters represented by the general formula [2] and lactones represented by the general formula [3] can be respectively reduced to alcohols represented by the general formula [4] and diols represented by the general formula [5] in the presence of the Group 8 (VIII) transition metal complex represented by the general formula [1], the base and hydrogen gas (Mode 1).

Further highly active catalytically active species can be prepared under combination of the Group 8(VIII) transition metal complex and the base which are preferable to each other (Mode 2).

Extremely highly active catalytically active species can be prepared under combination of the Group 8(VIII) transition metal complex and the base which are particularly more preferable to each other (Mode 3).

A further practical reduction method can be provided under combination of Modes 1 to 3 and the preferable used amount of the base (Mode 4).

A highly practical reduction method can be provided under combination of Modes 1 to 4 and the preferable pressure of hydrogen gas (Mode 5).

An extremely practical reduction method can be provided under combination of Modes 1 to 5 and the preferable reaction temperature (Mode 6).

EXAMPLES

Embodiments of the present invention will be specifically discussed with reference to Examples, in which the present invention is not limited to these Examples. Abbreviation symbols in Examples are as follows: NaOMe: sodium methoxide, Me: methyl group, Et: ethyl group, Ph: phenyl group, i-Pr: isopropyl group, Cp*: 1,2,3,4,5-pentamethylcyclopentadienyl group, $Et_2O$: diethyl ether, dioxane: 1,4-dioxane, THF: tetrahydrofuran, MeOH: methanol, IPA: isopropyl alcohol, t-BuOH: tert-buthyl alcohol, N—$C_2$*—N: optically active bidentate ligand in which two nitrogens are linked through two carbons, and N—$C_2$—N: bidentate ligand in which two nitrogens are linked through two carbons.

Examples 1 to 7

Experimental procedure of Example 3 will be described below as an representative example.

5 mg (0.01 mmol, 0.01 eq.) of Cp*RuCl[$Ph_2P(CH_2)_2NH_2$] represented by the following formula:

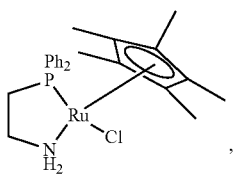

13.5 mg [0.25 mmol, 25 eq. (equivalent to ruthenium complex)] of sodium methoxide, 1 mL of tetrahydrofuran and 150 mg (1 mmol) of ethyl benzoate were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at 100° C. for 21 hours. As a result of gas chromatography analysis of a reaction-completed liquid, a conversion rate and an area percentage (GC area %) of benzyl alcohol as an object were respectively 100% and 99.6%. By-products 1 to 3 were not detected.

Concerning Examples 1, 2 and 4 to 7, the same procedure as in Example 3 was carried out upon changing the used amount of Cp*RuCl[Ph$_2$P(CH$_2$)$_2$NH$_2$], the used amount of sodium methoxide, the reaction solvent, the reaction temperature and the reaction time. Results of Examples 1 to 7 are tabulated in Table 1.

Examples 8 to 20

Experimental procedure of Example 8 will be described below as an representative example.

5 mg (0.01 mmol, 0.01 eq.) of Cp*RuCl[Ph$_2$P(CH$_2$)$_2$NH$_2$] represented by the following formula:

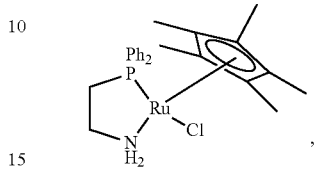

13.5 mg [0.25 mmol, 25 eq. (equivalent to ruthenium complex)] of sodium methoxide, 134 mg (1 mmol) of phthalide and 1 mL of isopropyl alcohol were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at 100° C. for 21 hours. As a result of gas chromatography analysis of a reaction-completed liquid, a conversion rate and an area percentage (GC area %) of 1,2-benzene dimethanol as an object were respectively 99.3% and 99.3%.

Concerning Examples 9 to 20, the same procedure as in Example 8 was carried out upon changing the used amount of sodium methoxide, the pressure of hydrogen gas, the reaction solvent and the reaction temperature. Results of Examples 8 to 20 are tabulated in Table 2.

TABLE 1

(note a;.)

PhC(O)OEt → PhC(O)OH
Cp*RuCl [Ph$_2$P(CH$_2$)$_2$NH$_2$]
NaOMe
H$_2$ (5 mPa)
solvent (1 M)

150 mg (1 mmol)

| Example | ruthenium complex | NaOMe[a] | solvent | temp. | time | conversion rate | object[b] | by-product-1[b,c,d] | -2 | -3 |
|---------|-------------------|----------|---------|-------|------|-----------------|-----------|---------------------|------|------|
| 1 | 0.005 eq | 100 eq | THF | 100° C. | 1 h | 30.4% | 8.5% | 13.0% | n.d. | n.d. |
| 2 | 0.02 eq | 25 eq | THF | 100° C. | 8 h | 93.2% | 89.9% | 1.4% | n.d. | n.d. |
| 3 | 0.01 eq | 25 eq | THF | 100° C. | 21 h | 100% | 99.6% | n.d. | n.d. | n.d. |
| 4 | 0.02 eq | 25 eq | IPA | 100° C. | 8 h | 99.9% | 96.7% | n.d. | 2.5% | n.d. |
| 5 | 0.01 eq | 25 eq | IPA | 100° C. | 21 h | 97.4% | 60.6% | n.d. | 36.0% | n.d. |
| 6 | 0.01 eq | 10 eq | IPA | 100° C. | 21 h | 18.4% | 11.6% | n.d. | 6.8% | n.d. |
| 7 | 0.01 eq | 25 eq | THF | 80° C. | 39 h | 63.3% | 51.8% | 3.3% | n.d. | 8.2% |

[a]equivalent to ruthenium complex
[b]GC area %.

[c]by-product -1     -2     -3.

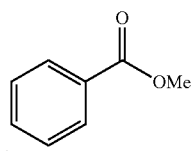 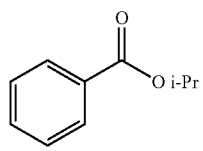 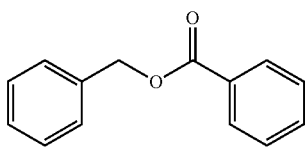

[d]n.d.: not detected.

TABLE 2

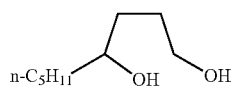

| Example | NaOMe[a] | H$_2$ | solvent | temp. | conversion rate | object[b] |
|---|---|---|---|---|---|---|
| 8 | 25 eq | 5 MPa | IPA | 100° C. | 99.3% | 99.3% |
| 9 | 25 eq | 5 MPa | MeOH | 100° C. | 99.5% | 99.0% |
| 10 | 25 eq | 5 MPa | t-BuOH | 100° C. | 97.8% | 97.2% |
| 11 | 25 eq | 5 MPa | dioxane | 100° C. | 99.2% | 97.2% |
| 12 | 25 eq | 5 MPa | toluene | 100° C. | 94.8% | 93.4% |
| 13 | 25 eq | 5 MPa | THF | 100° C. | 80.2% | 80.2% |
| 14 | 25 eq | 5 MPa | Et$_2$O | 100° C. | 98.4% | 98.0% |
| 15 | 20 eq | 5 MPa | IPA | 100° C. | 99.4% | 99.4% |
| 16 | 15 eq | 5 MPa | IPA | 100° C. | 96.2% | 96.2% |
| 17 | 25 eq | 4 MPa | IPA | 100° C. | 99.5% | 99.5% |
| 18 | 25 eq | 3 MPa | IPA | 100° C. | 98.4% | 98.4% |
| 19 | 25 eq | 5 MPa | IPA | 90° C. | 99.6% | 99.6% |
| 20 | 25 eq | 5 MPa | IPA | 80° C. | 98.2% | 96.8% |

[a]equivalent to ruthenium complex.
[b]GC area %.

Example 21

5 mg (0.01 mmol, 0.01 eq.) of Cp*RuCl[Ph$_2$P(CH$_2$)$_2$NH$_2$] represented by the following formula:

[chem. 11]

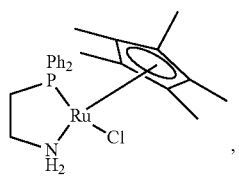

13.5 mg [0.25 mmol, 25 eq. (equivalent to ruthenium complex)] of sodium methoxide, 1 mL of isopropyl alcohol and 156 mg (1 mmol) of γ-nonanoic lactone were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at 100° C. for 21 hours. As a result of gas chromatography analysis of a reaction-completed liquid, a conversion rate and an area percentage (GC area %) of 1,4-nonane diol as an object were respectively 98.8% and 98.1%.

Result of Example 21 is shown in a scheme described below.

[chem. 12]

Example 21

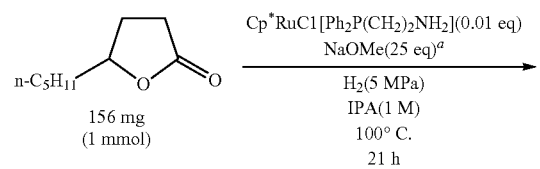

-continued

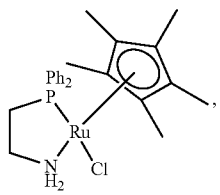

conversion rate 98.8%
GC area % 98.1%

[a] equivalent to ruthenium complex.

Example 22

5 mg (0.01 mmol, 0.01 eq.) of Cp*RuCl[Ph$_2$P(CH$_2$)$_2$NH$_2$] represented by the following formula:

[chem.13]

13.5 mg [0.25 mmol, 25 eq. (equivalent to ruthenium complex)] of sodium methoxide, 1 mL of isopropyl alcohol and 114 mg (1 mmol) of ε-caprolactone were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at 100° C. for 21 hours. As a result of gas chromatography analysis of a reaction-completed liquid, a conversion rate and an area percentage (GC area %) of 1,6-hexanediol as an object were respectively 84.6% and 78.6%.

Result of Example 22 is shown in a scheme described below.

bidentate ligand, the reaction temperature and the reaction time. Results of Examples 23 to 25 are tabulated in Table 3.

TABLE 3

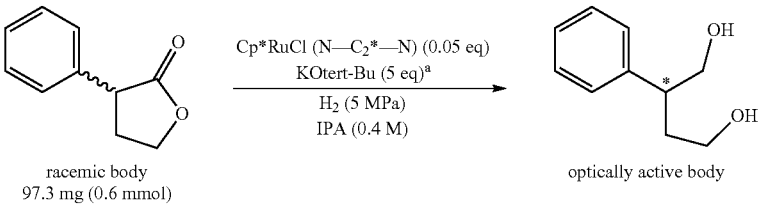 [SMILES: O=C1OCCC1c1ccccc1 ; OCCC(CO)c1ccccc1]

racemic body
97.3 mg (0.6 mmol)

optically active body

| Example | N—C$_2$*—N[b] | temp. | time | conversion rate | object |
|---|---|---|---|---|---|
| 23 | optically active bidentate ligand-1 | 80° C. | 48 h | 96% | 30% ee |
| 24 | optically active bidentate ligand-1 | 60° C. | 90 h | 96% | 35% ee |
| 25 | optically active bidentate ligand-2 | 80° C. | 48 h | 96% | 14% ee |

[a]equivalent to ruthenium complex.
[b]optically active bidentate ligand-1    optically active bidentate ligand-2.

[chem. 14]

Example 22

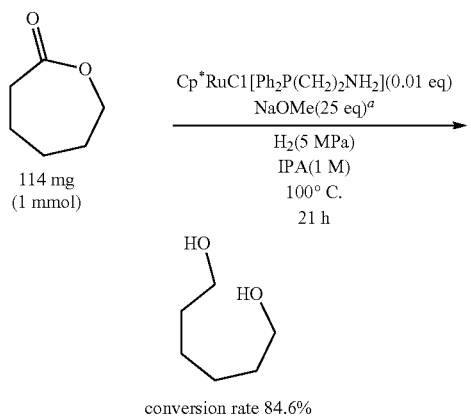

114 mg
(1 mmol)

conversion rate 84.6%
GC area % 78.6%

[a] equivalent to ruthenium complex.

Examples 23 to 25

Cp*RuCl(N—C$_2$*—N) (0.03 mmol, 0.05 eq.), 16.8 mg [0.15 mmol, 5 eq. (equivalent to ruthenium complex)] of potassium tert-butoxide, 1.5 mL of isopropyl alcohol and 97.3 mg [0.6 mmol (racemic body)] of α-phenyl-γ-butyrolactone were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at a certain temperature for a certain time. As a result of (chiral) gas chromatography analysis of a reaction-completed liquid, a conversion rate and an optical purity of 2-phenyl-1,4-butanediol (optically active body) as an object were measured.

Concerning Examples 23 to 25, a similar procedure was carried out upon changing N—C$_2$*—N as the optically active Example 26

Cp*RuCl(N—C$_2$—N) (0.01 mmol, 0.001 eq.), 135 mg [2.5 mmol, 250 eq. (equivalent to ruthenium complex)] of sodium methoxide, 4.5 mL of tetrahydrofuran and 1.24 g (10 mmol) of ethyl difluoroacetate were added into a Schlenk flask in an atmosphere of argon, and then freeze-deaeration was repeated three times. An obtained solution was transferred to a pressure reactor formed of stainless steel (SUS) having an inner tube formed of glass, by using a cannula. A gas inside the reactor was replaced with hydrogen gas five times, and a hydrogen pressure was set at 5 MPa, followed by stirring at 100° C. for 24 hours. As a result of gas chromatography analysis of a reaction-completed liquid, a conversion rate and an area percentage (GC area %) of 2,2-difluoroethanol as an object were respectively 66% and 100%.

Result of Example 26 is shown in a scheme described below.

[chem. 15]

Example 26

1.24 g
(10 mmol)

conversion rate 66%
GC area % 100%

-continued

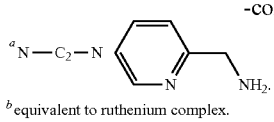
[b] equivalent to ruthenium complex.

The invention claimed is:
1. A method of respectively reducing esters represented by a general formula [2]

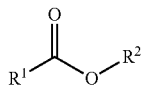
[2]

where
R$^1$ is an alkyl group, substituted alkyl group, alkenyl group, substituted alkenyl group, aromatic ring group or substituted aromatic ring group; and
R$^2$ is an alkyl group or substituted alkyl group, or lactones represented by a general formula [3]

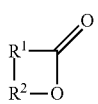
[3]

where
R$^1$—R$^2$ indicates that R$^1$ and R$^2$ of the esters represented by the general formula [2] are bonded by a covalent bond, to alcohols represented by a general formula [4]

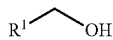
[4]

where
R$^1$ is the same as R$^1$ of the esters represented by the general formula [2], and diols represented by a general formula [5]

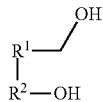
[5]

where
R$^1$—R$^2$ indicates that R$^1$ and R$^2$ of the esters represented by the general formula [2] are bonded by a covalent bond,
in the presence of
a Group 8 (VIII) transition metal complex represented by a general formula [1]

$$AMBC \qquad [1]$$

where
A is a cyclopentadienyl(Cp) group or 1,2,3,4,5-pentamethylcyclopentadienyl (Cp*) group;
M is Fe, Ru or Os;
B is halogen, carbon monoxide, acetonitrile, phenylisocyanide or triphenylphosphine; and
C is a bidentate ligand of a nitrogen-nitrogen (N—N) or phosphorus-nitrogen (P—N), base
and hydrogen gas (H$_2$).

2. A method of reducing esters or lactones as claimed in claim 1, wherein the Group 8 (VIII) transition metal complex represented by the general formula [1] is a Group 8 (VIII) transition metal complex represented by general formula [6]

$$Cp*RuX(P—C_2—N) \qquad [6]$$

where
Cp* is a 1,2,3,4,5-pentamethylcyclopentadienyl group;
X is halogen or acetonitrile;
P—C$_2$—N is a bidentate ligand in which phosphorus and nitrogen are linked through two carbons, and
the base is hydroxide or alkoxide of alkali metal.

3. A method of reducing esters or lactones as claimed in claim 2, wherein the Group 8 (VIII) transition metal complex represented by the general formula [6] is a Group 8 (VIII) transition metal complex represented by general formula [7]

$$Cp*RuCl[Ph_2P(CH_2)_2NH_2] \qquad [7]$$

where
Cp* is a 1,2,3,4,5-pentamethylcyclopentadienyl group;
Ph is a phenyl group, and
the base is alkoxide of alkali metal.

4. A method of reducing esters or lactones as claimed in claim 1, wherein the base is used in an amount of from 15 to 90 moles relative to 1 mole of the Group 8 (VIII) transition metal complex.

5. A method of reducing esters or lactones as claimed in claim 1, wherein the hydrogen gas (H$_2$) is at a pressure of from 3 to 7 Pa.

6. A method of reducing esters or lactones as claimed in claim 1, wherein a reaction temperature of from 80 to 150° C. is used.

* * * * *